United States Patent [19]
Mishiro

[11] Patent Number: 4,705,980
[45] Date of Patent: Nov. 10, 1987

[54] DRIVE CONTROL METHOD OF ULTRASONIC VIBRATOR

[75] Inventor: Shoji Mishiro, Kanagawa, Japan

[73] Assignee: Taga Electric Co., Ltd., Tokyo, Japan

[21] Appl. No.: 910,981

[22] Filed: Sep. 24, 1986

[30] Foreign Application Priority Data

Apr. 21, 1986 [JP] Japan ................. 61-91881

[51] Int. Cl.⁴ ............................................. H01L 41/08
[52] U.S. Cl. ..................................... 310/323; 310/317; 310/325
[58] Field of Search ......................... 310/314, 316–319, 310/323, 325

[56] References Cited

U.S. PATENT DOCUMENTS

| | | | |
|---|---|---|---|
| 4,484,099 | 11/1984 | Kawai et al. ......................... | 310/317 |
| 4,504,760 | 3/1985 | Yamamoto et al. ............. | 310/328 X |
| 4,510,411 | 4/1985 | Hakamata et al. ............... | 310/328 X |
| 4,562,373 | 12/1985 | Tokusima et al. ............... | 310/323 X |
| 4,620,121 | 10/1986 | Mishiro ................................. | 310/323 |
| 4,652,786 | 3/1987 | Mishiro ............................ | 310/328 X |

*Primary Examiner*—Mark O. Budd
*Attorney, Agent, or Firm*—Oblon, Fisher, Spivak, McClelland, & Maier

[57] ABSTRACT

In an ultrasonic vibrator provided such that its electrostrictive element is constituted of an electrostrictive element body polarized in the direction of its thickness, pairs of electrodes each thereof being peripherally divided into two segments formed on one face thereof, and a common electrode formed on the other face thereof, and metallic members shaped in such a form that will make the flexural resonant frequency and the axial resonant frequency equal are integrally fastened by means of a fastener onto both faces of one sheet or a plurality of sheets of the electrostrictive elements, the present invention is characterized in that a flexural driving output of inverted phase is applied to the respective electrodes forming the pairs in the electrostrictive member and a common axial driving output is applied to the respective electrodes in a superimposed manner, so that the vibrations in the axial direction and the flexural direction are individually controlled as if there are individually present an axially driven element and a torsionally driven element, and thereby, composite vibrational patterns are easily provided.

11 Claims, 14 Drawing Figures

DRIVE CONTROL METHOD OF ULTRASONIC VIBRATOR

FIELD OF THE INVENTION AND RELATED ART STATEMENT

The present invention relates to an ultrasonic vibrator generating ultrasonic vibration and more particularly to a drive control circuit for an ultrasonic vibrator making the ultrasonic vibrator to produce a composite vibration for use in a vibratory cutter, supersonic motor, and the like in a machine tool.

As a high-power ultrasonic vibrator in general, one called a Langevin type vibrator is widely used. The Langevin type vibrator is of such a structure that an annular electrostrictive element is sandwiched between metallic members and the whole is adapted to resonate as one body. The Langevin type vibrators can be broadly divided into two categories: one of the axial vibrator system in which an axial vibration is produced and the other of the torsional vibrator system in which a torsional vibration is produced around the axis. But, since the direction of vibration of these vibrators is limited to a single axial or torsional direction, these vibrators, in view of their vibrational pattern, are classified under the type of a unidirectional vibrator.

In this connection, there has been known means for forming, for example, an ultrasonic motor with the above described Langevin vibrator and make the same produce a composite vibration. As an example of it, there is known such means as described in Japanese Patent Laid-open No. 55-125052/1980. Namely, an axial vibrator is provided with a vibrating piece attached to its output end portion and a moving member such as a rotor is arranged with its normal line slightly inclined with reference to the axial direction of the vibrator and such that the vibrating piece is pressed against the rotor. Thereby, the end portion of the vibrating piece, relatively speaking makes an elliptical vibration and frictionally drives the rotor, and as a consequence of the foregoing, a composite vibration is produced by the unidirectional vibrator. The arrangement, however, has such a defect that when such a composite vibration is produced, the contact portion between the vibrating piece and the rotor severely wears out, and, also, a loud noise is thereby produced.

Figure 12:
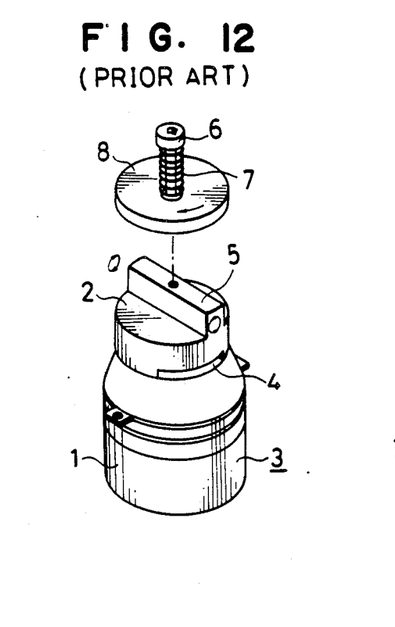
FIG. 12 is an exploded view in perspective of an example of the prior art.

As another example of producing a composite vibration by the use of the Langevin type vibrator, there has been known such a vibrator as shown in FIG. 12. In this case, a vibrator 3 is formed of an axial vibrator 1 and a torsional conversion member 2 integrally fastened together. In one surface of the torsional conversion member 2, there is formed a wide groove 4, and on the other face thereof, there is formed a beam shape protrusion 5 at a predetermined angle with the groove 4. And to the mentioned torsional conversion member 2 is attached a disk shape rotor 8 operably pressed thereto for rotation through a bolt 6 and a coil spring 7. With such construction, if an axial vibration is produced by the axial vibrator 1, the vibration is transmitted to the torsional conversion member 2. Then, an elliptical vibration is produced at the front end of the beam shape protrusion 5 of the torsional conversion member 2 in the direction as indicated by the arrow. And thereby, the rotor 8 rotates in the direction as indicated by the arrow. In such means, however, it is not possible to control the ellipticity of the elliptical vibration representing the vibrational pattern at the output end to be set to the optimum ellipticity for frictional driving. This is true because the ellipticity is automatically determined by the form of the torsional conversion member 2. Therefore, there is such a defect that it is not possible to reduce the wear on the surfaces of friction between the rotor 8 and the beam shape protrusion 5 or make the drive at the maximum torque efficiently performed. Also, there is a problem is that it is impossible to control the rotating direction of the rotor 8, because the rotating direction is also automatically determined by the form of the torsional conversion member 2.

Under these situations, a vibrator to be driven so as to separately generate an axial vibration and a torsional vibration thereby to make a composite vibration produced was invented and applied for patent by the present applicant, and the same is laid open in Japanese Patent Laid-open No. 61-28482/1986. That is, a torsional vibrator is provided at its nodal portion, at right angle with its axial direction, with a radial resonant member or a longitudinal resonant member, together with its driving element, integrally fastened thereto. Here, the resonant frequency of the radial resonant member, etc. is set to be the same as the torsional resonant frequency of the torsional vibrator. In the vibrator of the described structure, composite vibrational patterns at its output end are controlled by changing respective amplitudes, relative phase therebetween, or both the respective amplitudes and the relative phase. Thus, a wide variety of composite vibrations are provided by controlling the respective amplitudes and the relative phase thereby to make vibrations in the torsional direction and the axial direction individually produced. However, there is a problem in it that the radial resonant member or longitudinal resonant member occupies a relatively large portion of the volume of the entire vibrator and it is impossible to make it in a small size. Incidenttally, the present applicant applied for patent an ultrasonic motor utilizing such a vibrator which is laid open in Japanese Patent Laid-open No. 61-30972.

Figure 13:
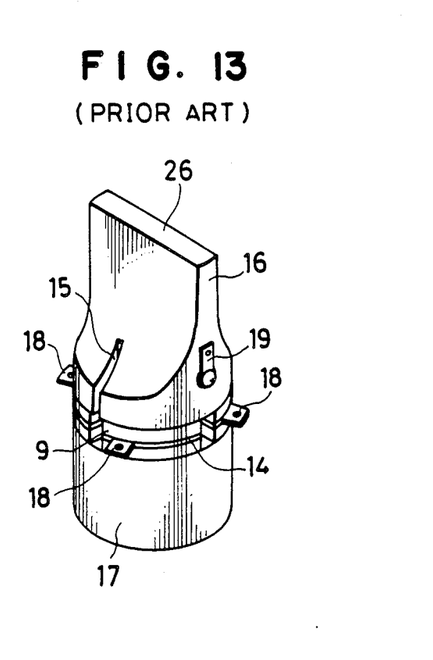
FIG. 13 is a perspective view of an ultrasonic vibrator already proposed by the present applicant.
Figure 14:
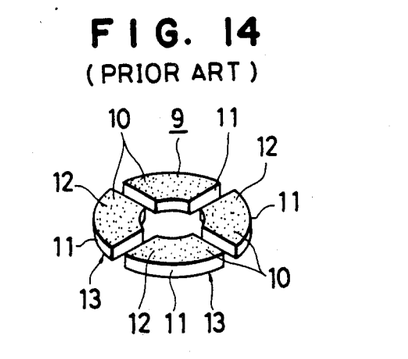
FIG. 14 is a perspective view of the electrostrictive element used in the above mentioned ultrasonic vibrator.

On the other hand proposals to provide small-sized vibrators with the function or providing various composite vibrations maintained as it is are detailed in Japanese patent application Nos. 60-266617, 60-291732/1985, etc. applied by the present applicant. The outline of the structure of the same will be described in the following. An electrostrictive element body polarized in the direction of its thickness is prepared. On one face thereof, there are formed two pairs of electrodes, each peripherally divided into two segments, and on the other face, there is formed a common electrode. And, onto both faces of such a sheet or a plurality of sheets of electrostrictive elements are integrally fastened metallic members by means of a fastener. A concrete example thereof is shown in Figs. 13 and 14. First, as shown in FIG. 14, an electrostrictive element 9 is formed of two sheets of electrode pairs 10 peripherally and annularly arranged. Each of the electrode pairs 10 is formed of two sheets of quarter segments, combined into a semicircular form, of an electrostrictive element body 11 polarized in the direction of its thickness, and there are formed electrodes 12 on one face thereof and a common electrode 13 on the other face. And, as shown in FIG. 13, there are provided two sheets of such electrostrictive elements 9 and a first metallic member 16, one of the above mentioned electrostrictive elements 9, an electrode plate 14, the other of the electrostrictive elements 9, and a second metallic member 17 are arranged in the named order and integrally fastened together by a bolt, or the like. Here, the first metallic member 16 is provided with two grooves 15 made in its axial direction, and these grooves 15 are positioned in between the above mentioned electrode pairs 10. And the front end portion of the cylindrical member of the first metallic member 16 is shaped as if shaved into a thin plate, and the front end of the thin plate is made to serve as an output end portion 26. On the other hand, the second metallic member 17 is shaped into a cylindrical form. And, the above mentioned electrode plate 14 is divided into segments corresponding to the electrodes 12 of the electrostrictive element 9 and arranged in contact with these electrodes 12, and a terminal 18 is drawn from each of the divided segments of the electrode plate 14. Further, the abovementioned first metallic member 16 is provided with a common electrode 19 connected with the above mentioned common electrode 13.

In the vibrator of the described construction, the pairs of the electrodes 12, i.e., the terminals 18 of the electrode plate 14, are diagonally connected in parallel and these electrodes are applied with A.C. driving outputs controlled for the amplitudes, or the relative phase, or both the amplitudes and the relative phase. Then, any form of composite vibration such as linear vibration, circular vibration, and elliptical vibration is produced at the output end portion 26. That is, since electrostrictive elements 9 expanding and contracting in the direction of their thickness are driven at shifted phases between peripherally adjoining elements, there is also produced a flexural vibration, and a composite vibration of the axial vibration and torsional vibration is thereby produced.

In the above described drive control method of the ultrasonic vibrator, the control of the ellipticity, for example, in an elliptical vibration is achieved by the controlling the relative phase. However, the amplitude serving as the reference also suffers a change, and therefore, it becomes necessary to control also each amplitude. That is, it becomes necessary to perform a synthesized control for both the axial and the torsional directions, and this causes the control as a whole to become difficult.

OBJECT AND SUMMARY OF THE INVENTION

A primary object of the present invention is the provision of a drive control method of an ultrasonic vibrator capable of easily controlling a composite vibration produced by an axial vibration and a torsional vibration.

The present invention, to solve the above mentioned problems, applies electrodes forming pairs in an electrostrictive element with a phase-inverted flexural driving output and also apply them, in a superimposed manner, with a common axial driving output. And through controlling amplitudes or relative phase or both the amplitudes and the relative phase of the respective driving outputs, for example, of the driving voltages, it is enabled to produce a linear vibration, circular vibration, or elliptical vibration, which is composed of a torsional vibration or a vibration in the direction at a right angle with the axis and an axial vibration, in any direction on the output end face of the vibrator. In this case, by applying the respective driving outputs in a superimposed manner, the axial vibration and the flexural vibration are individually produced the same as in the case where an axially driven element and a torsionally driven element are individually present, and therefore, a composite vibrational pattern is easily provided.

DESCRIPTION OF THE PREFERRED EMBODIMENT

An embodiment of the present invention will be described with reference to FIG. 1 to FIG. 11. Prior to the description of the embodiment, meaning of the major terms will be made clear. The torsinal vibrations or the vibrations in the direction at a right angle with the axis in the ultrasonic vibrator in the present invention are all flexural resonant vibrations in view of their type of generation. This flexural resonant vibration was the vibration in the direction at a right angle to the axis at the output end portion in the case of the later discussed vibrators described in Japanese patent application No. 60-252526 and Japanese patent application No. 60-281170/1985 already applied by the present applicant. Likewise the vibration in the torsional direction at the output end portion in the case of the other later discussed vibrators is already applied for patent by the present applicant. Accordingly, in the present specification, each of them will be called 'the vibration in the direction at a right angle with the axis' and 'the torsional vibration', and when referring to the generating mechanism of the vibrations, they will be called 'the flexural vibration'.

Figure 3:
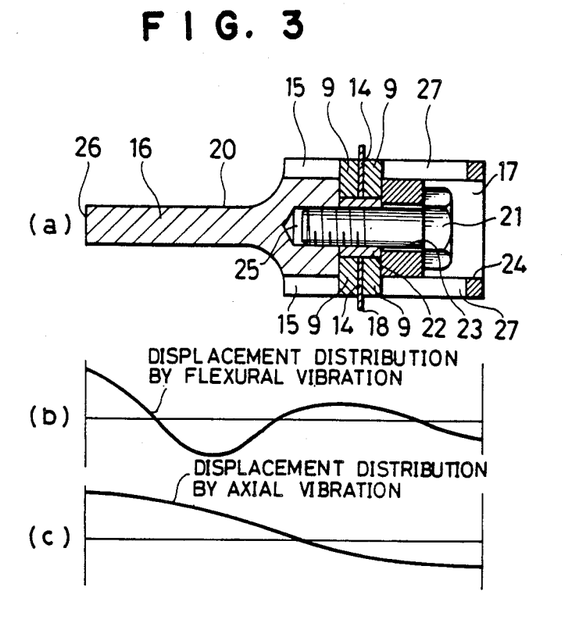
FIG. 3 is a sectional view of the same.

Now, construction of the ultrasonic vibrator 20 for use in the present embodiment will be described. In the present embodiment, the ultrasonic vibrator as shown in FIGS. 13 and 14 is used. Therefore, like parts to those shown in FIGS. 13 and 14, for example, are denoted by like reference numerals and description of the same are omitted here. At first, as shown in FIG. 3 (a), two sheets of electrostrictive elements 9 with an electrode plate 14 interposed therebetween are integrally fastened together with two metallic members 16 and 17 by means of a bolt 21 as a fastener. In more detail, there is a pipe-formed insulating material 22 is interposed between the inner peripheral hole of the electrostrictive element 9 and the outer periphery of the bolt 21. And, the metallic member 17 is provided with a through hole 23 and a large-diametered recess portion 24, and the metallic member 16 is provided with a female screwed portion 25. Further, the second metallic member 17 is provided with two grooves 27 in the axial direction, corresponding to the grooves 15 made in the first metallic member 16, in such a way that the grooves are ended before they reach the end.

With the vibrator 20 of the described construction, at first, all the electrode plates 14 (hence, the electrodes 12) are connected in parallel and an A.C. voltage is applied thereto with reference to the common terminal 19 and the frequency thereof is adjusted to the axial resonant frequency. Then, the vibrator 20 resonates in the axial direction and the output end portion 26 produces a resonant vibration with the maximum displacement. The displacement distribution at this time becomes as shown in FIG. 3(c) and the resonance is made at ½ wavelength. Then, the electrode plates 14 are diagonally connected in parallel and A.C. voltages of opposite phases to each other are applied thereto with reference to the common terminal 19, and the frequency is adjusted to the flexural resonant frequency. Then, the vibrator 20 resonates in the torsional direction and the diametral ends of the output end portion 26 produce a resonant vibration with the maximum displacement. This is because the states of expansion and contraction of the segments of the electrostrictive element 9 are reversed between the adjoining segments, and thereby the metallic members 16 and 17 are caused to produce a flexural vibration giving rise to a torsional vibration at the output end portion 26. The displacement distribution at this time becomes as shown in FIG. 3(b) and the resonance is made at 3/2 wavelengths. Incidentally, the deformed section in the longitudinal direction of the first metallic member 16 is so given that the amplitude of the axial vibration may be enhanced, the amplitude of the torsional vibration may be enhanced, and the resonant frequencies in the axial direction and the torsional direction may agree with each other. And, the grooves 15 and 27 made in the metallic members 16 and 17 are useful for releasing the harmful stress produced in the course of the flexural vibration.

Figure 1:
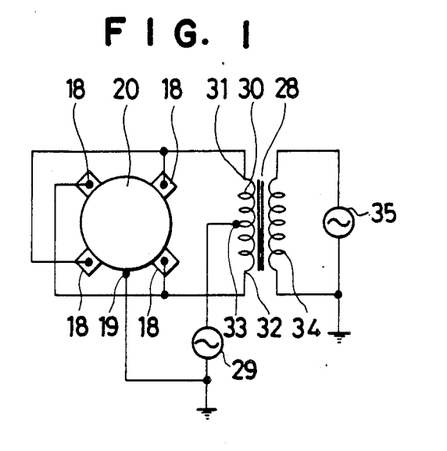
FIG. 1 is a connection diagram for driving a vibrator describing an embodiment of the present invention.
Figure 2:
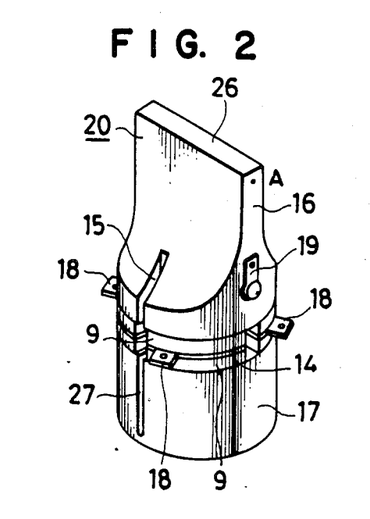
FIG. 2 is a perspective view of a vibrator.

In the present embodiment, the flexural driving voltage and the axial driving voltage are applied in a superimposed manner, and as the means for achieving that, a transformer 28, for example, is used to drive the vibrator 20. The connection diagram in that case is shown in FIG. 1. First, the common terminal 19 of the vibrator 20 is grounded connected to the earth side of the driving power source 29 for the axial vibration. And, the electrode plates 14 (the terminals 18) are alternately connected in parallel and they are connected to both ends 31 and 32 of the secondary coil 30 of the transformer 28. To the center tap 33 of the secondary coil 30 of the transformer 28 is connected the above mentioned driving power source 29. And, to the primary coil 34 is connected a driving power source 35 for the flexural vibration with one end thereof grounded.

Figure 4:
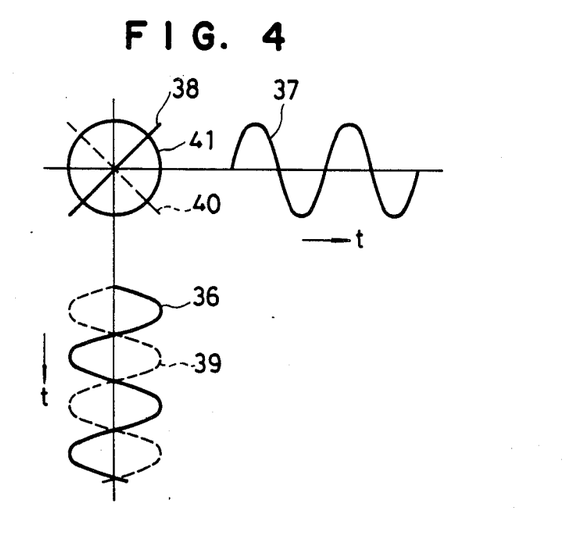
FIG. 4 is a graph showing vibrational patterns composed of the axial vibration and torsional vibration.

In the drive by means of the described connection, it is possible to provide various patterns of composite vibrations by changing driving conditions. At first, the driving power sources 29 and 35 are driven at the same frequency of the resonant frequency and in phase, the vibration produced by the point A on the periphery of the output end portion 26 of the vibrator 20 becomes as shown by the straight line 38. This is because, as shown in FIG. 4, the axial vibration 36 and the torsional vibration 37 are at a right angle with each other and in phase. Then, if the relative phase is reversed 180°, the axial vibration becomes as shown by the dotted line 39 and the composite vibration becomes as shown by the dotted line 40, and thereby, the vibrating direction is turned through the angle of 90°. If, further, the relative phase is changed to 90°, the composite vibration becomes a circular vibration 41. In this case, according to whether the relative phase is leading or lagging by 90°, the direction of the rotation is reversed. Further, by changing the relative amplitude, an elliptical vibration is produced, and in this case, by a combination of the relative amplitude and relative phase, an inclined elliptical vibration is provided. As hitherto known well, by orthogonal composition of sinusoidal vibrations, a wide variety of composite vibrational patterns can be provided.

States of vibrations of the vibrator when driven with the amplitude, the relative phase, or both the amplitude and the relative phase controlled are shown in FIG. 5 to FIG. 11.

Figures 5, 6:
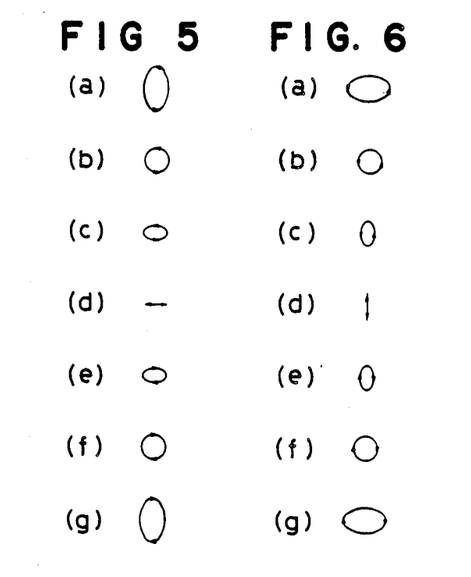
FIGS. 5 to 11 are graphs showing variations of vibrational patterns.

First, the vibrator is driven only by the driving power source 29 with the voltage of the driving power source 35 is kept at zero. Then, the point A at the peripheral of the output end portion 26 vibrates in the axial direction as shown in FIG. 5(d). Then, as the amplitude of the driving power source 35 is increased with its relative phase to the driving power source 29 set at 90°, the vibrational pattern varies from a horizontally elongated ellipse, through a circle, to a vertically elongated ellipse as shown in FIGS. 5 (c), (b) and (a). If the relative phase is changed to −90°, the rotating direction is reversed from the previous case and the vibrational pattern varies as shown in FIGS. 5(e), (f), and (g). Namely, FIG. 5 shows the vibrational patterns provided when the axial vibration is kept constant and the torsional vibration at the relative phases of ±90° is changed.

Then, only the voltage of the driving power source 35 is applied while the voltage of the driving power source 29 is kept at zero. Now, the point A makes a torsional vibration in the direction at a right angle with the axis as shown in FIG. 6(d). Then, as the amplitude of the driving power source 29 is increased, vibrational patterns in which the ellipticities and rotating directions are changed according to the amplitudes and the relative phases ±90° are provided as shown in FIGS. 6(c), (b), and (a), or FIGS. 6(e), (f), and (g). Namely, FIG. 6 shows the vibrational patterns provided when the torsional vibration is kept constant and the axial vibration at the relative phases of ±90° is changed.

Figures 7, 8:
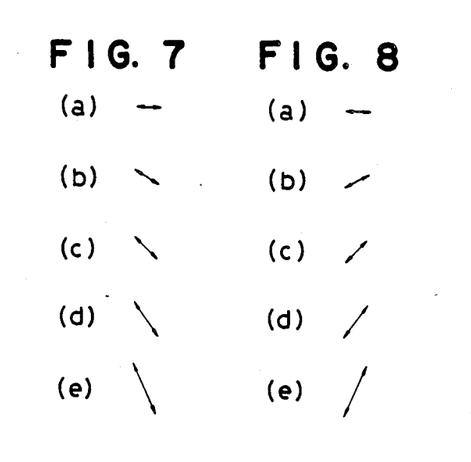

Then, the driving voltage of the driving power source 29 is kept constant, and the amplitude of the driving voltage of the driving power source 35 is increased from zero, while the phase thereof is kept in phase with the driving power source 29. Then, the axial vibration varies its angle of inclination and at the same time increases its amplitude of vibration as shown in FIGS. 7(a) to (e). And, if the phase between both the driving power sources is inverted and the amplitude of the driving voltage of the driving power source 35 is increased from zero, the axial vibration varies its angle of inclination in the opposite direction to that in FIG. 7 and at the same time increases its amplitude of vibration as shown in FIGS. 8(a) to (e). Namely, FIG. 7 shows the vibrational patterns provided when the axial vibration is kept constant and the amplitude of the torsional vibration is changed, and FIG. 8 shows the vibrational patterns provided when the axial vibration is kept constant and the amplitude of the torsional vibration is changed with the phase of the torsional vibration inverted.

Figure 9:
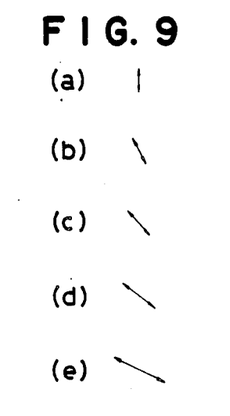
Figure 10:
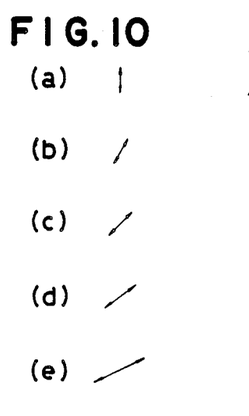

Then, the torsional driving voltage of the driving power source 35 is kept constant and the amplitude of the axial driving voltage of the driving power source 29 is increased from zero, while its phase is kept in phase with the driving power source 35. Now, the torsional vibration increases its amplitude of vibration while changing its angle of inclination as shown in FIGS. 9(a) to (e). And, if the phase between both the driving voltages is inverted and the amplitude of the driving voltage of the driving power source 29 is increased from zero, then, the torsional vibration increases its amplitude of vibration while changing its angle of inclination in the opposite direction to that in the above case as shown in FIGS. 10(a) to (e). Namely, FIGS. 9 and 10 show, conversely to FIGS. 7 and 8, the vibrational patterns in the case where the torsional side is kept constant and the axial side is changed.

Figure 11:
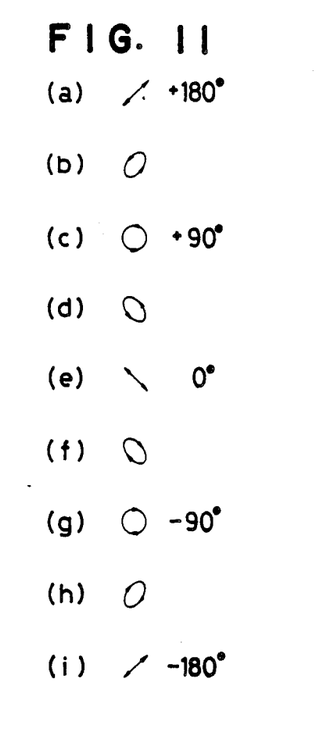

Finally, the driving voltages that will make the amplitudes of vibration in the axial direction and the torsional direction equal are applied by the driving power sources 29 and 35 and the relative phase between both the driving voltages is set to 0°. Then, a linear vibration at the angle of 45° with the axis is provided as shown in FIG. 11(e). In this case, by controlling the relative phase, such vibrational patterns are provided as an inclined ellipse (d), a circle (c), an inclined ellipse in the opposite direction (b), and a straight line inclined in the opposite direction (a) are provided. And, if the relative phase is inverted, such vibrational patterns in the opposite rotating direction as shown in FIGS. 11(f), (g), (h), and (i) are provided in like manner.

As described in the foregoing, by controlling the amplitude of each of the axial driving voltage and the torsional driving voltage by the driving power sources 29 and 35 and the relative phase therebetween, a wide variety of composite vibrational patterns such as a straight line, inclined straight line, ellipse, inclined ellipse, and a circle. And, it is enabled to individually control one driving power source 29 as that for the component in the axial direction and the other driving power source 35 as that for the component in the torsional direction, or in the direction at a right angle with the axis. That is, it is made possible to make the controlling in the manner as if there are individually present both an axial vibrator and a torsional vibrator. And thereby, it is easily achieved to control the vibrational pattern such that, for example, the ellipticity is controlled under the condition in which the amplitudes are kept constant. Specifically, such control is made easy by the use of the transformer 28.

Although the present embodiment was described taking, as an example, a vibrator whose output end portion 26 was shaped in the I form, the present invention is not limited to such a vibrator but applicable in like manner to other vibrators invented by the present inventor and already proposed in Japanese patent application Nos. 60-252526, 60-266617, 60-281170, 60-291732/1985 and 61-12822/1986. The vibrator described in Japanese patent application No. 60-252526 is such that its electrostrictive element is constituted of an electrostrictive element body polarized in the direction of its thickness, electrodes divided into two pieces formed on one face thereof, and a common electrode formed on the other face thereof, and metallic members are integrally fastened onto both faces of the electrostrictive element with a fastener. The vibrator descibed in Japanese patent application No. 60-266617 is such that its electostrictive element is formed by providing an electrostrictive element body polarized in the direction of its thickness with a plurality of sets of electrode pairs disposed on one side thereof, and the same is made integral with a vibrating member having leg portions peripherally divided in the same number as the number of the electrode pairs. The vibrator described in Japanese patent application No. 60-281170 is such that its electrostrictive element is constituted of an electrostrictive element body polarized in the direction of its thickness, four or more even number of electrodes radially formed on one face thereof with an insulating portion interposed therebetween, and a common electrode formed on the other face, and metallic members are integrally fastened onto both sides of the electrostrictive element by a fastener. The vibrator described in Japanese patent application No. 60-291732 is such that its electrostrictive element polarized in the direction of its thickness and provided with electrodes divided into two pieces is joined with a metallic member, and an output end portion provided with at least three contact legs radially formed thereon is formed on the metallic member. Finally, the vibrator described in Japanese patent application No. 61-12822 is such that its electrostrictive element polarized in the direction in its thickness and provided with electrodes divided into two pieces is joined with a metallic member, and the metallic member is provided with grooves made therein along dividing lines corresponding to the number of electrodes in pairs.

Although the driving power sources were described in the present embodiment as driving voltages controlled for their amplitude or relative phase, either of the hitherto known constant voltage driving and constant current driving can be used in the present driving system, in which case, the constant voltage driving is preferred to be used at parallel resonant frequencies and the constant current driving is preferred to be used at series resonant frequencies.

What is claimed is:

1. A drive control method for an ultrasonic vibrator having an electrostrictive element constituted by a electrostrictive element body polarized in the direction of its thickness and pairs of electrodes each electrode of said pairs being peripherally divided into two segments formed on one face thereof and a common on the other face thereof, said vibrator further having metallic members shaped in such a form that the flexural resonant frequency and the axial resonant frequency are equal and wherein said metallic members are integrally fastened by means of a fastener onto both faces of at least one sheet of said electrostrictive element body, the drive control method of said ultrasonic vibrator comprising the steps of:

applying flexural driving outputs to each of the respective electrodes forming the pairs in said electrostrictive member wherein the flexural drive output applied to one of each of said pair is phase inverted when compared to the flexural drive output applied to the other of each of said pairs;

applying a common axial driving output to each of said electrodes respectively wherein said common axial driving output is superimposed with said flexural driving output.

2. A drive control method according claim 1 wherein the steps of providing driving outputs includes the step of providing driving voltages having amplitude control.

3. A drive control method according to claim 1 wherein the steps of providing driving outputs includes the step of providing driving voltages having phase control.

4. A drive control method according to claim 1 wherein the steps of providing driving outputs includes the step of providing driving voltages having both amplitude and phase control.

5. A drive control method according to claim 1 wherein the steps of providing driving outputs includes the step of providing drive voltages wherein the relative phase between the respective drive voltages is 90° and wherein the amplitudes of the respective voltages are controlled.

6. A drive control method according to claim 1 wherein the steps of providing drive outputs further include the step of providing driving a current.

7. A drive control method for an ultrasonic vibrator having an electrostrictive element constituted by a electrostrictive element body polarized in the direction of its thickness and pairs of electrodes each electrode of said pairs being peripherally divided into two segments formed on one face thereof and a common electrode formed on the other face thereof, said vibrator further having metallic members shaped in such a form that the flexural resonent frequency and the axial resonant frequency are equal and wherein said metallic members are integrally fastened by means of a fastener onto both faces of at least one sheet of said electrostrictive element body, the drive control method of said ultrasonic vibrator comprising the steps of:

applying a flexural driving voltage to the respective electrodes forming said pairs in said electrostrictive element wherein the step of applying a flexural driving voltage includes the step of applying said driving voltage to the primary coil of a transformer wherein both ends of the secondary coil of said transformer are connected to the respective electrodes forming the pairs in said electrostrictive element;

applying an axial driving voltage to the center point of said secondary coil of said transformer so that a common axial driving voltage is applied to the respective electrodes in a superimposed manner.

8. The method according to claim 7 wherein the steps of providing driving voltages includes the step of providing amplitude control driving voltages.

9. The method according to claim 7 wherein the steps of providing driving voltages includes the step of providing driving voltages having controlled phases.

10. The method according to claim 7 wherein the steps of providing driving voltages includes the step of providing driving voltages having both controlled amplitudes and controlled relative phase.

11. The method according to claim 7 wherein the steps of providing driving voltages includes the step of providing driving voltages having a respective phase between voltages of 90° and having the amplitudes of said voltages being controlled.

* * * * *